United States Patent
Yamagishi et al.

(10) Patent No.: US 6,615,678 B2
(45) Date of Patent: Sep. 9, 2003

(54) EXHAUST GAS SAMPLING DEVICE

(75) Inventors: Yutaka Yamagishi, Kyoto (JP); Satoshi Ohtsuki, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/921,530

(22) Filed: Aug. 3, 2001

(65) Prior Publication Data

US 2002/0020232 A1 Feb. 21, 2002

(30) Foreign Application Priority Data

Aug. 9, 2000  (JP) .................................. 2000-241565

(51) Int. Cl.$^7$ ................................................ G01N 1/00
(52) U.S. Cl. .................................................. 73/863.11
(58) Field of Search ....................... 73/863.03, 863.11, 73/863.12, 864.73, 23.31–23.33

(56) References Cited

U.S. PATENT DOCUMENTS

| 3,794,909 A | | 2/1974 | Smith | |
| 5,456,124 A | * | 10/1995 | Colvin | ..................... 73/863.11 |
| 5,604,319 A | * | 2/1997 | Kohsaka et al. | ......... 73/863.11 |
| 6,148,656 A | * | 11/2000 | Breton | ....................... 73/23.31 |

FOREIGN PATENT DOCUMENTS

| DE | 31 36 646 A1 | 4/1983 |
| DE | 3800219 A1 | 7/1989 |
| DE | 39 18 154 A1 | 12/1990 |

OTHER PUBLICATIONS

Ströhlein, Labor–, Mess– und Umwelttechnik, Apr. 12, 2000; Umweltschutz–Messgeräte in Modultechnik, pp. 4,6, 7.

* cited by examiner

Primary Examiner—Robert Raevis
(74) Attorney, Agent, or Firm—Brooks & Kushman P.C.

(57) ABSTRACT

An exhaust gas sampling device is provided. An exhaust gas sampling tube for sampling part of the exhaust gas is connected to an exhaust tube in which the exhaust from a source of the exhaust gas flows, and a downstream side of the exhaust gas sampling tube is connected to a dilution tunnel. The device further includes a temperature control mechanism. A temperature of the exhaust gas sampling tube is controlled with the temperature control mechanism based on a temperature of the exhaust gas flowing in the exhaust tube.

12 Claims, 2 Drawing Sheets

EXHAUST GAS SAMPLING DEVICE

BACKGROUND OF THE INVENTION

1. Field of the Invention

The present invention relates to an exhaust gas sampling system used in a system of measuring PM in the exhaust gas, which performs the quantitative analysis of PM (Particulate Matter such as soot) included in the gas discharge from a diesel engine or the like mounted on an automobile.

2. Background Art

As one of the methods for measuring PM in the above described exhaust gas, there is a method according to the filter gravimetric method. Then, in the case of performing the measurement of this kind, an exhaust gas sampling system of the partial dilution total sampling system is used, where for example, part of the exhaust gas is divided and introduced into the dilution tunnel as the sample gas, and this sample gas (exhaust gas) is diluted by the air for dilution in the dilution tunnel, and the total amount or a partial amount of this diluted exhaust gas is arranged to flow in the measurement flow passage provided in the filter for the collection of PM.

The above described exhaust gas sampling system has previously been constructed as shown in FIG. 2. That is, in FIG. 2, reference numeral 1 denotes a diesel engine mounted on an automobile as the source of the exhaust gas, and reference numeral 2 denotes an exhaust tube as an exhaust gas flow passage communicating with this. Reference numeral 3 denotes an exhaust gas sampling tube inserted and connected to the exhaust tube 2 for sampling part of the exhaust gas G flowing in the exhaust tube 2, and the downstream side thereof is connected to a dilution tunnel 4 that dilutes the total amount of the sampled exhaust gas G. Reference numeral 5 denotes a supply tube of the dilution air A connected to the upstream side of this dilution tunnel 4.

Reference numeral 6 denotes a gas flow passage which is connected to the downstream side of the dilution tunnel 4 and in which the diluted sample gas S flows, and the downstream side of this gas flow passage 6 is branched into two flow passages 7, 8, and to the respective flow passages 7, 8, filters 9, 10 for collecting PM included in the sample gas S are provided, and one flow passage 7 is constructed as a measurement gas flow passage for letting the exhaust gas flow when sampling PM, and furthermore, the other flow passage 8 is constructed as a by-pass flow passage for letting the exhaust gas flow when not sampling PM, respectively. Furthermore, among the filters 9, 10, one filter 9 is the measuring filter, and the other filter 10 is the dummy filter.

Reference number 11 denotes a three-way solenoid valve as flow passage switching means provided on the downstream side of the sample gas flow passage 7 and the by-pass flow passage 8, and the downstream side thereof is connected to a gas flow passage 12, and to this gas flow passage 12, a suction pump, for example, a Roots-blower pump 13 that can change the suction power by the rotational speed control, and a flow meter, for example, a Venturi flow meter 14 that has a high measuring accuracy are provided in this order. Furthermore, as the flow meter 14, a mass flow meter containing a laminar flow meter or a hot wire type flow meter can also be used.

In the exhaust gas sampling device with the above described construction, in the steady operation state where the rotational speed and the torque of the engine 1 are nearly constant, the diluted sample gas S flows in the measurement gas flow passage 7, and in the case of the transient operation state where the rotational speed and the torque of the engine 1 are changed, or when the rotational speed or the torque of the engine 1 is changed to move to a different rotational speed or a torque, the flow passage is switched so that the diluted sample gas S may flow in the by-pass flow passage 8.

The main components of PM included in the exhaust gas G discharged from the engine 1 are the dry soot (hereafter, referred to simply as soot) that is the carbon grain, the soluble organic fraction (hereafter, referred to simply as SOF), and the sulfates (matter made of the sulfur oxide connected to water). Then, the temperature of the exhaust gas G discharged from the engine 1 and flowing in the exhaust tube 2 reaches 400–600° C. at most, and under such a high temperature, the components of PM such as the above described soot, SOF, or sulfates are gaseous. On the other hand, in the gas sampling device of the partial dilution total sampling system, the exhaust gas sampling tube 3 has, for example, a length of about 0.05 to 1.5 m and an inside diameter of about 6 to 10 mm, and the flow rate of the gas flowing in this is 2 to 20 L/minute, which is a comparatively small flow rate.

Accordingly, when the exhaust gas G flowing in the exhaust tube 2 flows into the above described exhaust gas sampling tube 3, if there is a difference in temperature between the inner wall of the exhaust gas sampling tube 3 and the exhaust gas G, a so-called pholetic loss may occur, in which the PM component in the exhaust gas G is attached to the inner wall of the exhaust gas sampling tube 3, or the PM component that has been once attached is removed again and gasified. Thus, when the PM component is attached or separated again at the inner wall of the exhaust gas sampling tube 3, a deviation occurs in the weight of PM collected by the measuring filter 9, especial the SOF component which is easily vaporized by the temperature of the wall because SOF is evaporated by high temperature and a large error is included in the measurement result of PM measured by the filter gravimetric method or the like.

Therefore, in the prior art, the exhaust tube 2 has previously been warmed to a proper temperature by using the heat of the exhaust gas in the engine warming up operation before the test, and in the meantime, the exhaust gas sampling tube 3 has been heated at a certain temperature, or the dilution tunnel 4 has also been temperature-controlled to have a proper temperature.

However, as mentioned above, even when the exhaust gas sampling tube 3 is temperature-controlled, the above described deviation has not sufficiently been restrained. The reason is that even in the steady state operation, in the actual test, several different rotational speeds and torques are combined in turn, and in the test in the transient state, they are all the more in such a situation, and the rotational speed of the engine 1 is not always constant. Furthermore, the amount of the exhaust gas G from the engine 1 is not always constant, and the temperature of the exhaust gas G is also not always constant.

SUMMARY OF THE INVENTION

It is an object of the present invention to provide an exhaust gas sampling device, which restrains the gasifying of PM included in the exhaust gas by preventing the PM from being attached to or separated again from the inner wall of the exhaust gas sampling tube and as a result of that, suitably helps the PM to be sampled accurately.

In carrying out the above object, an exhaust gas sampling device is provided and is made in such a way where an exhaust gas sampling tube for sampling part of the exhaust gas is connected to an exhaust tube in which the above described exhaust gas from the source of the exhaust gas flows, wherein the temperature of the above described exhaust gas sampling tube is controlled according to a certain relational expression in which the temperature of the exhaust gas flowing in the above described exhaust tube is a parameter.

Further, in carrying out the above object, an exhaust gas sampling device is provided and is made in such a way where an exhaust gas sampling tube for sampling part of the exhaust gas is connected to an exhaust tube in which the above described exhaust gas from the source of the exhaust gas flows, and the downstream side of this exhaust gas sampling tube is connected to a dilution tunnel, wherein a temperature sensor for measuring the temperature of the exhaust gas flowing in the interior thereof is provided to the above described exhaust tube and on the other hand, to the above described exhaust gas sampling tube, a temperature control mechanism for controlling the temperature thereof is provided, and the above described temperature control mechanism is acted on the basis of the output of the above described temperature sensor, and the temperature of the above described exhaust gas sampling tube is controlled according to a certain relational expression in which the temperature of the exhaust gas flowing in the above described exhaust tube is a parameter.

In the exhaust gas sampling device of this invention, it is possible that the temperature of the exhaust gas is sequentially measured and the temperature of the tube wall of the exhaust gas sampling tube is temperature-controlled in the state of the following the temperature of the above described measured exhaust gas, and therefore, it is possible to effectively restrain the attaching and the re-separation of PM caused by the difference between the temperature of the above described exhaust gas and the above described tube wall temperature, and the sampling of PM and the measuring accuracy of the fixed quantity thereof can largely be improved.

DETAILED DESCRIPTION OF THE PREFERRED EMBODIMENT(S)

Figure 1:
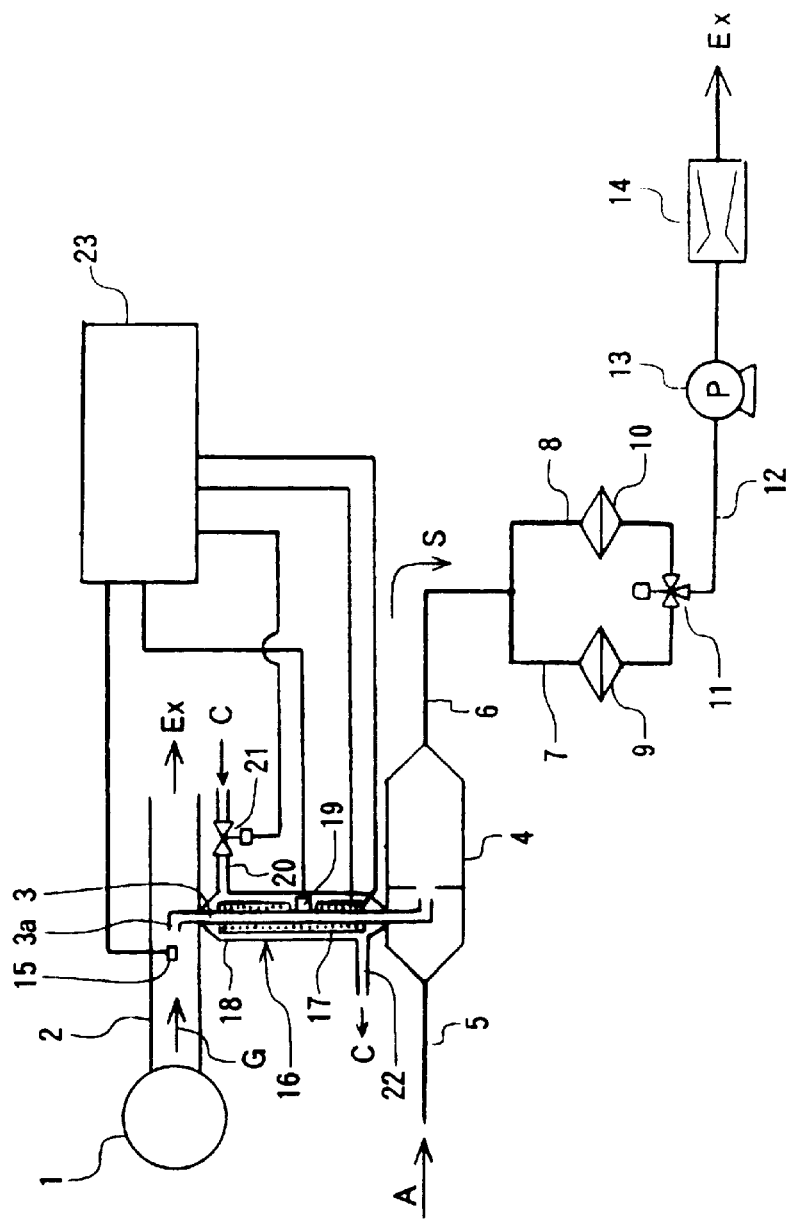
FIG. 1 is a figure schematically showing one example of the structure of the exhaust gas sampling device of this invention.
Figure 2:
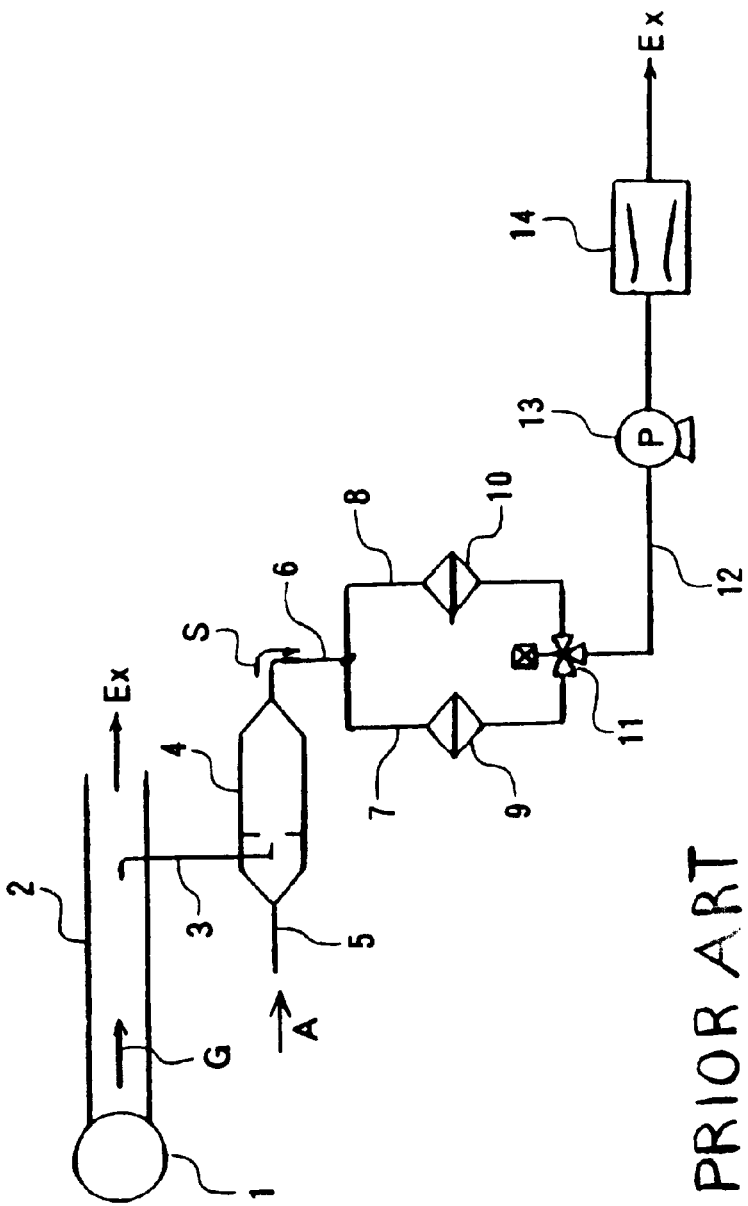
FIG. 2 is a figure for explaining the prior art.

The preferred embodiments of this invention will be described while referring to the drawings. FIG. 1 is a figure schematically showing one example of the exhaust gas sampling device of this invention, and in this figure, the same reference numerals as the reference numerals in FIG. 2 denote the same parts, and therefore, the description thereof will be omitted. In the present invention, dilution tunnel 4 may be omitted.

In FIG. 1, reference numeral 15 denotes a temperature sensor provided in the exhaust tube 2, and for example, it consists of a thermistor. This temperature sensor 15 is a sensor for measuring the temperature of the exhaust gas G discharged from the engine 1 that is the source of the exhaust gas, and it is provided at a position near the sampling hole 3a of the exhaust gas sampling tube 3 and on the slightly upstream side thereof.

Then, reference numeral 16 denotes a temperature control mechanism for temperature-controlling of the exhaust gas sampling tube 3, and it comprises: a heater 17 winded and provided around the exhaust gas sampling tube 3; a cooling device 18 provided to cover the heater 17 and the exhaust gas sampling tube 3 on the outside of this heater 17; and a temperature sensor 19 consisting of, for example, a thermistor of detecting the temperature of the tube wall of the exhaust gas sampling tube 3. Reference numeral 20 denotes a coolant inlet tube for introducing a proper coolant (for example, cooling water or gas) C to the cooling device 18, and it is provided with an on-off valve 21 such as a solenoid valve. Furthermore, reference numeral 22 denotes a coolant outlet tube for introducing the coolant C from the cooling device 18. These coolant inlet tube 20 and coolant outlet tube 22 are connected to the coolant supply source and the coolant temperature control machine that are not shown in the figure, respectively.

Reference numeral 23 denotes a temperature control device, and to this temperature control device 23, the output of the temperature sensors 15, 19 is inputted, and in the meantime, on the basis of the input thereof, the electric power supply control to the heater 17 and the on-off control of the on-off valve 20 are performed.

In the exhaust gas sampling device with the above described construction, the temperature of the exhaust gas G discharged from the engine 1 is measured sequentially by the temperature sensor 15, and the measurement result thereof is sent sequentially to the temperature control device 23. Then, in the temperature control device 23, the target temperature of the exhaust gas sampling tube 3 is sequentially set by using the above described detected temperature of the exhaust gas G as a parameter, and the exhaust gas sampling tube 3 is heated or cooled.

The fact that the target temperature of the exhaust gas sampling tube 3 is sequentially set by using the above described detected temperature of the exhaust gas G as a parameter means, for example, the following fact. Now, in the case where the above described temperature of the exhaust gas G is less than 200° C., the temperature control is performed so that the temperature of the exhaust gas sampling tube 3 becomes equal to the temperature of the exhaust gas G. That is, with the exhaust gas sampling tube 3, the temperature sensor 19 is provided, and the temperature of the exhaust gas G detected by the above described temperature sensor 15 are compared, and in the case where the temperature of the exhaust gas sampling tube 3 is lower, the heater 17 is made to generate heat, and the exhaust gas sampling tube 3 is heated.

On the contrary, in the case where the temperature of the exhaust gas sampling tube 3 is higher, the on-off valve 21 is opened, and the coolant is supplied to the cooling device 18, and the exhaust gas sampling tube 3 is cooled.

Furthermore, in the case where the temperature of the above described exhaust gas G is 200° C. or more, for example, a value made by multiplying that numerical value with a certain constant is set as the target temperature of the exhaust gas sampling tube 3, and in order to attain this target temperature, the heater 17 or the cooling device 18 is operated. It should be noted that the above description is provided as an example only, and it should be apparent enough without clearly mentioning that this invention is not limited to the above description.

Furthermore, in the above described embodiments, it is arranged that the cooling device 18 is provided to the temperature control mechanism 16, and the exhaust gas sampling tube 3 is forced to be cooled, but it is also possible that the cooling device 18 is not provided and natural cooling is performed.

As described above, in the exhaust gas sampling device of this invention, the temperature of the exhaust gas is sequentially measured, and the temperature of the exhaust gas sampling tube is controlled according to a certain relational expression in which the temperature of the above described measured exhaust gas is a parameter, and therefore, the temperature of the tube wall of the exhaust gas sampling tube can be temperature-controlled in the state of following the temperature of the exhaust gas. Accordingly, the attaching, gasification, and reseparation of PM caused by the difference between the temperature of the exhaust gas and the temperature of the tube wall of the exhaust gas sampling tube can effectively be restrained, and the sampling of PM and the measuring accuracy of the fixed quantity thereof can largely be improved.

Then, this invention is useful particularly in the exhaust gas sampling device of the partial dilution total sampling system, in which part of the exhaust gas is separated by using an exhaust gas sampling tube capable of neglecting the influence of the exhaust gas and is introduced into the dilution tunnel as sample gas, and this sample gas (exhaust gas) of a comparatively small flow rate is diluted by the air for dilution in the dilution tunnel, and the total amount of this diluted exhaust gas is arranged to flow in the measurement passage having the PM collecting filter provided.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An exhaust gas sampling device in which an exhaust gas sampling tube for sampling part of the exhaust gas is connected to an exhaust tube in which the exhaust from a source of the exhaust gas flows, the device further comprising:

a temperature control mechanism wherein a temperature of the exhaust gas sampling tube is controlled with the temperature control mechanism based on a temperature of the exhaust gas flowing in the exhaust tube.

2. The device of claim 1 wherein the temperature of the exhaust gas sampling tube is controlled with the temperature control mechanism so as to follow the temperature of the exhaust gas flowing in the exhaust tube.

3. The device of claim 2 wherein the temperature control mechanism further comprises:

a heater at the exhaust gas sampling tube.

4. The device of claim 3 wherein the temperature control mechanism further comprises:

a cooling device at the exhaust gas sampling tube.

5. The device of claim 1 further comprising:

a temperature sensor for measuring the temperature of the exhaust gas flowing in the exhaust tube.

6. An exhaust gas sampling device in which an exhaust gas sampling tube for sampling part of the exhaust gas is connected to an exhaust tube in which the exhaust from a source of the exhaust gas flows, and a downstream side of the exhaust gas sampling tube is connected to a dilution tunnel, the device further comprising:

a temperature sensor for measuring a temperature of the exhaust gas flowing in the exhaust tube; and means for controlling a temperature of the exhaust gas sampling tube wherein the temperature of the exhaust gas sampling tube is controlled based on the temperature of the exhaust gas flowing in the exhaust tube.

7. The device of claim 6 wherein the temperature of the exhaust gas sampling tube is controlled so as to follow the temperature of the exhaust gas flowing in the exhaust tube.

8. The device of claim 7 wherein the means for controlling further comprises:

a heater at the exhaust gas sampling tube.

9. The device of claim 8 wherein the means for controlling further comprises:

a cooling device at the exhaust gas sampling tube.

10. An exhaust gas sampling method in which an exhaust gas sampling tube for sampling part of the exhaust gas is connected to an exhaust tube in which the exhaust from a source of the exhaust gas flows, and a downstream side of the exhaust gas sampling tube is connected to a dilution tunnel, the method comprising:

controlling a temperature of the exhaust gas sampling tube based on a temperature of the exhaust gas flowing in the exhaust tube.

11. The method of claim 10 wherein the temperature of the exhaust gas sampling tube is controlled so as to follow the temperature of the exhaust gas flowing in the exhaust tube.

12. The method of claim 10 further comprising:

measuring the temperature of the exhaust gas flowing in the exhaust tube.

* * * * *

UNITED STATES PATENT AND TRADEMARK OFFICE
CERTIFICATE OF CORRECTION

PATENT NO.    : 6,615,678 B2
DATED         : September 9, 2003
INVENTOR(S)   : Yutaka Yamagishi and Satoshi Ohtsuki It is certified that error appears in the above-identified patent and that said Letters Patent is hereby corrected as shown below:

<u>Title page,</u>
Item [*] Notice the adjustment under "0 days" should be -- 245 days. --.

Signed and Sealed this

First Day of June, 2004

JON W. DUDAS
*Acting Director of the United States Patent and Trademark Office*